United States Patent
Berlinger et al.

(10) Patent No.: US 12,232,865 B2
(45) Date of Patent: Feb. 25, 2025

(54) COMPUTATION OF A BREATHING CURVE FOR MEDICAL APPLICATIONS

(71) Applicant: Brainlab AG, Munich (DE)

(72) Inventors: Kajetan Berlinger, Munich (DE); Hagen Kaiser, Munich (DE)

(73) Assignee: Brainlab AG, Munich (DE)

( * ) Notice: Subject to any disclaimer, the term of this patent is extended or adjusted under 35 U.S.C. 154(b) by 153 days.

(21) Appl. No.: 16/957,430

(22) PCT Filed: Jul. 8, 2019

(86) PCT No.: PCT/EP2019/068282
§ 371 (c)(1),
(2) Date: Jun. 24, 2020

(87) PCT Pub. No.: WO2021/004620
PCT Pub. Date: Jan. 14, 2021

(65) Prior Publication Data
US 2023/0035624 A1   Feb. 2, 2023

(51) Int. Cl.
*A61B 5/113* (2006.01)
*A61B 5/00* (2006.01)
(Continued)

(52) U.S. Cl.
CPC .......... *A61B 5/1135* (2013.01); *A61B 5/0077* (2013.01); *A61B 5/1122* (2013.01);
(Continued)

(58) Field of Classification Search
CPC .......... A61N 5/1049; A61N 2005/1062; A61N 2005/1051; A61N 2005/1059;
(Continued)

(56) References Cited

U.S. PATENT DOCUMENTS

2008/0049896 A1* 2/2008 Kuduvalli ............ A61N 5/1049
378/65
2008/0177280 A1* 7/2008 Adler ...................... A61B 90/10
901/41
(Continued)

FOREIGN PATENT DOCUMENTS

EP   1563799 A1   8/2005
WO   2008/024463 A2   2/2008
(Continued)

OTHER PUBLICATIONS

X. Gao, E. Shahhaidar, C. Stickley and O. Boric-Lubecke, "Respiratory Angle of Thoracic Wall Movement During Lung Ventilation," in IEEE Sensors Journal, vol. 16, No. 13, pp. 5195-5201, Jul. 1, 2016, doi: 10.1109/JSEN.2016.2561242, hereto referred as Gao (Year: 2016).*

(Continued)

*Primary Examiner* — Michael R Bloch
*Assistant Examiner* — Elina Sohyun Jang
(74) *Attorney, Agent, or Firm* — Tucker Ellis LLP

(57) ABSTRACT

A computer-implemented medical method of determining a breathing signal of a patient is disclosed. The method includes determining a motion trajectory of a structure associated with at least one body part of the patient, the motion trajectory being indicative of a respiratory movement of the structure, acquiring surface data representative of a position of a surface region of the patient, computing an intersection of the determined motion trajectory and the acquired surface data, and determining a breathing signal of the patient based on the computed intersection. The breathing signal is indicative of a breathing state of the patient.

20 Claims, 3 Drawing Sheets

(51) Int. Cl.
*A61B 5/11* (2006.01)
*A61N 5/10* (2006.01)

(52) U.S. Cl.
CPC .......... *A61B 5/1127* (2013.01); *A61B 5/7289* (2013.01); *A61N 5/1049* (2013.01)

(58) Field of Classification Search
CPC ... A61B 5/1135; A61B 5/1127; A61B 5/1128; A61B 5/0077; A61B 5/1122; A61B 5/7289; G06T 7/248; G06T 7/74; G06T 7/20
See application file for complete search history.

(56) References Cited

U.S. PATENT DOCUMENTS

| | | | |
|---|---|---|---|
| 2012/0226152 A1* | 9/2012 | Porikli | A61B 5/1128 600/427 |
| 2014/0236036 A1* | 8/2014 | de Haan | G06T 7/0012 600/534 |
| 2015/0085072 A1* | 3/2015 | Yan | A61N 5/1048 348/43 |
| 2016/0210747 A1* | 7/2016 | Hay | G06F 16/7335 |
| 2018/0308247 A1* | 10/2018 | Gupta | G06T 7/62 |

FOREIGN PATENT DOCUMENTS

| | | |
|---|---|---|
| WO | 2016/087058 A1 | 6/2016 |
| WO | 2018219609 A1 | 12/2018 |

OTHER PUBLICATIONS

Udaya Wijenayake et al: "Real-Time External Respiratory Motion Measuring Technique Using an RGB-D Camera and Principal Component Analysis", Sensors, published on Aug. 2017, 23 pages.
International Search Report and Written Opinion for corresponding International Application No. PCT/EP2019/068282, dated Jul. 8, 2019. 12 Pages.

* cited by examiner

COMPUTATION OF A BREATHING CURVE FOR MEDICAL APPLICATIONS

RELATED APPLICATION DATA

This application is a national phase application of International Application No. PCT/EP2019/068282 filed Jul. 8, 2019, the contents of which are incorporated herein by reference.

RELATED APPLICATION DATA

This application is a national phase application of International Application No. PCT/EP2019/068282 filed Jul. 8, 2019, the contents of which are incorporated herein by reference.

FIELD OF THE INVENTION

The present invention relates to a computer-implemented medical method of determining a breathing signal and/or a breathing curve of a patient, a corresponding computer program or program, a non-transitory program storage medium storing such a program and a computer for executing the program, as well as a medical system comprising an electronic data storage device and the aforementioned computer.

TECHNICAL BACKGROUND

For certain medical applications, particularly radiotherapy applications or treatments, such as e.g. treatments of extracranial tumors, targets and/or tissue, it may be desirable to have respiratory information about a respiratory movement of the patient and/or certain body parts thereof in real-time or near real-time available.

In certain radiotherapy treatments, for example, the tissue to be treated can move with respiration, as is the case e.g. for lung or liver treatments. Therein, a breathing curve may be used during radiation treatment planning to identify the position of the tissue to be treated. Therein, the position of the tissue to be treated in dependence of a breathing state of the patient can, for instance, be identified based on medical images, such as e.g. X-ray images, MRI images, CT images or scans, 4DCT scans or the like. Apart from the treatment planning procedure, the breathing curve can be used during the actual treatment for determining and/or predicting the position of the tissue to be treated and/or a target position, which should be covered by a radiation beam, while the patient may be freely breathing.

Another exemplary radiotherapy application where respiratory information is used, is the treatment of a breast, particularly the left breast. In those treatments, the patient's heart should preferably be kept out of the radiation beam path due to the heart's high sensitivity to ionizing radiation. To ensure this, the treatment technique "Deep Inspiration Breath-Hold" (DIBH) may applied, wherein the patient can be guided to the planned depth of inspiration based on the breathing curve (and/or based on a breathing signal) of the patient.

Apart from that, information about respiratory movement of a patient and/or a breathing state of the patient may be valuable for many other radiotherapy applications as well as other medical applications. For example, it may be desirable to know about the breathing motion (or respiratory movement) to be able to differ these vital motions from unintended patient movements.

The present invention can be used for various medical applications or treatments. Particularly, the present invention can be used for radiation therapy applications (or radiotherapy applications), including both treatment planning and the actual treatment, e.g. in connection with a system for image-guided radiotherapy such as VERO® and ExacTrac®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, an exemplary and short description of some features of the present invention is given which shall not be understood to limit the invention only to the features or a combination of the features described in this section. Rather, the following section is provided for illustrative purposes of the present disclosure. The invention is defined in the independent claims, wherein further exemplary embodiments are defined in the dependent claims and the following description.

The disclosed method relates to a computer-implemented medical method of determining a breathing signal and/or a breathing curve of a patient. Alternatively or additionally, the disclosed method relates to a computer-implemented data processing method for determining a breathing signal and/or a breathing curve. Therein, the breathing signal may be indicative and/or representative of a breathing state of the patient. For instance, the breathing signal may refer to and/or correlate with an amplitude of the patient's breathing curve at a certain time or time instant.

According to the method, a motion trajectory of a structure, such as e.g. a point, area and/or volume of arbitrary shape and/or geometry, which is associated with at least one body part, e.g. an anatomical body part, of the patient is determined, wherein the motion trajectory describes a respiratory movement of the structure and/or contains information related thereto. In the context of the present disclosure, the term respiratory movement may refer to a breathing motion, e.g. a motion, movement and/or displacement caused by or related to a breathing activity of the patient. Accordingly, the motion trajectory may be descriptive of a movement of the structure in space caused by and/or related to a breathing, breathing activity and/or respiratory movement of the patient and/or the at least one body part the structure is associated with. In a further step, surface data are acquired, such as e.g. images and/or image data, which can describe or contain information related to a position of a surface region of the patient. Based thereon, an intersection of the determined motion trajectory and the acquired surface data is computed. The computed intersection can then be used to determine and/or derive the breathing signal.

Generally, this allows to determine the breathing signal and/or the breathing curve with high accuracy and precision. Further, the breathing signal and/or the breathing curve can be determined in real-time or near real-time. The determined breathing signal and/or the breathing curve can then further be used to advantage for medical applications or treatments, particularly for radiotherapy applications, including radiation treatment planning and radiation treatment.

In radiation treatments, for instance, a position of a tissue to be treated in space can be determined based on the breathing signal and/or the breathing curve. Also, the patient can e.g. be guided to a planned depth of inspiration in a DIBH based radiation treatment.

It should be noted, however, that the present invention is not limited to radiotherapy applications. Rather, the invention can be used to advantage in any other medical application, in which respiratory information can be of value. This includes surgical applications as well as the mere monitoring of a patient's breathing activity.

GENERAL DESCRIPTION OF THE INVENTION

In this section, a description of the general features of the present invention or disclosure is given for example by referring to possible embodiments of the invention. Specifically, various aspects of the present disclosure are described in the following. It should be noted, however, that any feature, element and/or step described in the following with respect to one aspect of the present disclosure equally applies to any other aspect of the present disclosure.

As stated hereinabove, it may be desirable for certain medical applications, e.g. for certain radiotherapy applications and/or treatments, to efficiently, quickly and reliably determine a breathing signal and/or a breathing curve of a patient.

This is achieved by the subject matter of the independent claims, wherein further embodiments are incorporated in the dependent claims and the following description.

According to a first aspect, a computer-implemented medical method of determining a breathing signal and/or a breathing curve of a patient is provided. Alternatively or additionally, the method according to the first aspect may refer to a computer-implemented medical data processing method. The method comprises the following steps:

determining a motion trajectory of a structure associated with at least one body part of the patient, wherein the motion trajectory is indicative, descriptive and/or representative of a respiratory movement of the structure;

acquiring surface data representative of a position of a surface region of the patient;

computing, calculating and/or determining an intersection of the determined motion trajectory and the acquired surface data; and determining a breathing signal and/or a breathing curve of the patient based on the computed intersection, wherein the breathing signal is indicative of a breathing state of the patient.

Accordingly, the breathing signal and/or a breathing curve of the patient can be determined, calculated and/or computed with high precision and accuracy based on intersecting the motion trajectory and the surface data. Inter alia, this advantageously allows determining the breathing signal and/or the breathing curve real-time and/or near real-time. Such determination of the breathing signal and/or the breathing curve may be of particular advantage in many medical applications, for example, radiotherapy applications and/or radiation therapy applications, including radiation treatment planning as well as the actual treatment.

Further, as the breathing signal and/or the breathing curve can be determined (at least predominantly) based on a data processing approach or technique, it may not necessarily be required (although possible) to use a device specifically dedicated for this purpose. In turn, this allows retrofitting existing medical devices and/or medical systems with the method according to the invention in a cost-efficient manner, e.g. without requiring any (or at least no substantial) hardware modifications.

In the context of the present disclosure, the structure associated with the at least one body part may refer to a point, area, volume and/or region of arbitrary shape and/or geometry. The structure can, for example, move and/or be displaced in relation with, in correspondence with, in accordance with and/or in dependence of a respiratory movement of the patient and/or of the at least one body part. For example, the structure may refer to an anatomical structure of the patient and/or of the at least one body part. Further, the structure can be part of, representative of and/or refer to the at least one body part. The structure and/or the at least one body part can be located (at least partly) inside the patient's body, such as e.g. a sternum. Alternatively or additionally, the structure and/or the at least one body part can be located at least partly on or at a surface and/or an outer contour of the patient, such as e.g. a surface region and/or surface portion of the patient. It should be noted, however, that the structure does not necessarily have to refer to a structure of the patient itself. Rather, the structure can be any patient-external structure, which may be spaced apart from the patient's surface and move in correspondence with the patient's respiratory movement, such that the motion trajectory, a movement and/or displacement of the structure can be indicative of and/or correlate with the respiratory movement of the patient and/or the at least one body part. For instance, the structure can also refer to and/or comprise a marker or marker device.

Further, the step of determining the motion trajectory of the structure can refer to and/or comprise acquiring the motion trajectory and/or data (e.g. trajectory data) related to, indicative of, descriptive of and/or representative of the motion trajectory. The motion trajectory and/or the corresponding (trajectory) data can for example be retrieved from a data storage. Further, the motion trajectory and/or the corresponding (trajectory) data can be pre-defined and/or can be determined based on capturing, analysing and/or processing structure data representative of a position of the structure during respiratory movement of the patient, as will be described in more detail hereinafter.

Generally, the motion trajectory can refer to an arbitrary trajectory, e.g. a two-dimensional or three-dimensional trajectory in space, along which at least a part of the structure and/or at least a part of the at least one body part moves and/or is displaced due to the respiratory movement of the patient. The motion trajectory (and/or corresponding data) can approximate and/or be indicative of the movement and/or displacement of the structure caused by the patient's breathing (i.e. the respiratory movement of the structure). Accordingly, the motion trajectory can be indicative of a direction, in which the structure is displaced (and/or moved) during breathing, and/or a distance, by which the structure is displaced (and/or moved) during breathing.

For instance, the motion trajectory can refer to and/or describe a linear and/or rectilinear movement of the structure in one or more spatial directions. Accordingly, the motion trajectory can refer to and/or be defined at least partly by a motion axis, e.g. a rectilinear motion axis. Generally, such motion axis can be a vertical or non-vertical axis with respect to a patient's coordinate system and/or reference system, wherein the patient's vertical axis is parallel to an anterior-posterior direction of the patient. Alternatively or additionally, the motion trajectory can refer to and/or describe a curvilinear movement of the structure. Also, a part of the motion trajectory can be rectilinear and a further part can be curvilinear. Further, the motion trajectory and/or corresponding (trajectory) data may be given in an arbitrary coordinate (or reference) system, e.g. the patient's coordinate (or reference) system or a coordinate (or reference) system of a medical system.

In the context of the present disclosure, the surface data may, for example, refer to image data and/or images. It should be noted that, however, that the surface data can refer to any type of image data, including optical image data, infrared image data, marker image data, x-ray image data, CT data, MRI data and/or data captured by means of any other imaging modality (and/or using any imaging method, e.g. as described in the "definitions section" hereinafter). Generally, the surface data may be descriptive and/or indicative of a position, a location and/or a course of the surface region of the patient in space, e.g. at a certain time and/or time instant during the breathing motion. Accordingly, the surface data may comprise time information and/or the surface data may refer to time-related surface data. Further, acquiring the surface data may comprise retrieving the surface data, e.g. from a data storage, and/or capturing the surface data. By way of example, the surface data may be given as and/or refer to a point cloud (or data point cloud) in space. Further, the surface data may be given in an arbitrary coordinate system and/or reference system, e.g. the patient's reference system or a reference system of a medical system.

In the context of the present disclosure the step of computing the intersection of the determined motion trajectory and the acquired surface data may refer to computing an intersection of the surface region as represented by the surface data with the motion trajectory. The intersection may be computed and/or calculated in space. In other words, computing the intersection may comprise determining intersection data indicative of one or more spatial coordinates of the intersection of the surface region and the motion trajectory. For this purpose, the motion trajectory and the surface data may be given in the same coordinate (or reference) system. Also, the surface region described by the surface data and/or the motion trajectory may be represented and/or approximated by a mathematical function and/or representation, based on which the intersection can be computed. E.g. the surface region may be approximated based on interpolating the surface data and/or based on deriving the mathematical function and/or representation for the surface region from the surface data. Further, it should be noted that the intersection and/or corresponding intersection data may comprise time information. Accordingly, the intersection and/or corresponding intersection may be time-related.

Generally, the surface region can refer to a (2D or 3D) portion and/or area of the patient's surface. The surface region may move and/or be displaced in correspondence and/or accordance with a respiratory movement of the patient. Accordingly, a position and/or location of the surface region in space, e.g. at a certain time instant, can be indicative of a breathing state, a breathing activity and/or a depth of inspiration of the patient (e.g. at the certain time instant).

Further, it should be noted that the surface region, optionally, can refer to and/or be part of the at least one body part the structure is associated with. Accordingly, the at least one body part can comprise and/or can be the surface region, and vice versa. Likewise, the structure can be associated with and/or relate to the surface region. For example, the structure can refer to a portion (and/or part) of or the entire surface region.

The structure and the body part, however, can differ at least partly from the surface region. For instance, the body part can be an abdominal wall, such that the motion trajectory describes a movement thereof, while the surface region can be arranged adjacent to and/or cover the sternum.

As stated above, a position of the surface region in space can be indicative of a breathing state, a breathing activity and/or a depth of inspiration of the patient, also the computed intersection can comprise information about and/or provide a measure for the patient's breathing state, breathing activity and/or depth of inspiration. This allows determining and/or deriving the breathing signal from the computed intersection. In the context of the present disclosure, the breathing state, the breathing activity and/or the depth of inspiration of the patient may refer to a point on the patient's breathing curve at a certain time and/or time instant, wherein the breathing curve can be given as e.g. a breathing amplitude over time (corresponding to a depth of inspiration over time). During regular breathing, the breathing curve usually is a sinusoidal, periodic or quasi-periodic curve. Accordingly, the breathing signal, may be indicative of, descriptive of, representative of, and/or correlate with the breathing amplitude (and/or depth of inspiration) at a certain time and/or time instant. In other words, the breathing signal can represent an amplitude (or breathing amplitude) of the breathing curve at a certain time and/or time instant. Further, the breathing signal can optionally be time-related and/or contain time information.

It should be noted that according to the present disclosure the breathing signal can refer to and/or be given by breathing data describing the breathing amplitude (e.g. at a certain time and/or time instant). Alternatively or additionally, the breathing signal may refer to an electrical signal indicative of the breathing amplitude (e.g. at a certain time and/or time instant). Therein the breathing amplitude may be any measure or quantity suitable for describing the patient's breathing activity, breathing state and/or depth of inspiration. For instance, the breathing amplitude may be a measure for an inhaled volume, a residual volume, a displacement of at least one body part of the patient due to respiratory movement or the like. Further, the breathing amplitude of the breathing curve may be given in absolute or relative values. It should be noted that the step of determining the breathing signal may comprise processing, transforming and/or analysing the intersection and/or intersection data. However, the breathing signal can also be given by the intersection and/or intersection data itself.

In the following, the first aspect of the present disclosure is re-phrased and summarized. The respiratory movement, i.e. a movement and/or displacement due to respiratory (movement and/or respiration) of the patient, of a structure that is associated with at least a body part of the patient and/or that moves during respiration, is described and/or approximated by the motion trajectory. The motion trajectory can, for example, describe the displacement in space, e.g. a periodic displacement in space, of the structure and/or the at least one body part caused by the breathing of the patient. Therein, the motion trajectory can be pre-defined and/or it can be determined in a data processing approach, e.g. during a learning phase. Further, based on surface data, the motion trajectory is intersected with a surface region and/or a surface of the patient. Thereby, the breathing signal resembling the patient's breathing state, breathing activity, depth of inspiration and/or breathing amplitude can be obtained an/or computed. Overall, this allows for an efficient, fast, accurate and reliable determination of the breathing signal, which can then be used in assisting a medical application and/or medical treatment.

According to an embodiment, determining the motion trajectory of the structure comprises defining a motion axis approximating the respiratory movement, the motion and/or the displacement of at least a part of the structure, e.g. in one or more spatial directions. Generally, the motion axis may be descriptive and/or indicative of a movement and/or displacement of the at least part of the structure and/or the at least one body part in at least one spatial direction. The motion axis may be predefined and/or e.g. given by a mathematical function and/or spatial coordinates. Alternatively or additionally, the motion axis may be defined by a user input. Further, the motion axis may be rectilinear and/or may be descriptive of one or more movement components of the respiratory movement of the at least part of the structure and/or the at least one body part. Therein, the motion axis may be parallel to a vertical axis of the patient, i.e. a vertical axis in the patient coordinate system and/or reference system parallel to an anterior-posterior direction of the patient. Alternatively, the motion axis may be tilted and/or skew with respect to the vertical axis of the patient. Generally, this allows to take various movement components, e.g. in various spatial directions, of the structure and/or the at least one body part into account.

In the context of the present disclosure, a movement component of the structure may refer to a movement and/or displacement of the structure in one spatial direction. The movement component may, for example, be defined by a spatial direction, in which the structure is displaced and/or moved during breathing. Alternatively or additionally, the movement component may be defined by a vector (or vector component), e.g. taking a distance, by which the structure is displaced and/or moved during breathing, into account.

It should be noted that depending on which body part the structure is associated with, the corresponding respiratory movement may have different movement components. For instance, some body parts may primarily move or be displaced in anterior-posterior direction with almost no movement component in cranial-caudal direction, while this may be reversed for other body parts. Accordingly, by approximating the actual respiratory movement of the structure with the motion axis, the breathing signal can be individually determined with high precision based on the individual movement of any structure and/or body part of the patient.

According to an embodiment, the motion trajectory is indicative of the respiratory movement, the motion and/or the displacement of at least a part of the structure in anterior-posterior direction and in cranial-caudal direction of the patient. In other words, the motion trajectory may be indicative of the respiratory movement, the motion and/or the displacement of at least a part of the structure parallel to a vertical direction and parallel to a longitudinal direction of the patient. Generally, this can allow to determine the breathing signal, the breathing state and/or the breathing activity of the patient with high precision and accuracy, particularly if the structure and/or the at least one body part move and/or are displaced in vertical and longitudinal direction during breathing. Therein, the vertical direction of the patient may correspond to the anterior-posterior direction and the longitudinal direction may correspond to the cranial-caudal direction.

According to an embodiment, the motion axis and a vertical axis parallel to the anterior-posterior direction of the patient enclose an angle of about 35° to about 55°, preferably about 40° to about 50°. In other words, the motion axis may be tilted with respect to the patient's vertical axis, e.g. in cranial-caudal direction. By tilting the motion axis, the respiratory movement of the structure and/or the body part may be approximated in at least two spatial directions, which may allow to increase a precision of the breathing signal According to an embodiment, determining the motion trajectory comprises acquiring a sequence of at least two temporally successive structure data, wherein each structure data is representative, indicative and/or descriptive of a position of at least a part of the structure and/or the at least one body part in a breathing cycle of the patient. Generally, the breathing cycle may refer to a part of the breathing curve over at least a part of a breathing period, e.g. comprising an inhaling and/or an exhaling phase. The sequence of structure data may refer to a series, time series and/or set of at least two structure data acquired and/or captured at different times. Accordingly, the sequence of structure data can comprise first structure data indicative of a first position of the structure in space at a first time instant and second structure data indicative of a second position of the structure in space at a second time instant different from the first time instant. For instance, based on the sequence of structure data, the structure and/or the position thereof can be tracked over time to determine the motion trajectory. In other words, determining the motion trajectory can comprise tracking the structure and/or the position thereof in the sequence of structure data. Generally, this allows to determine the movement of the structure with high precision, thereby also increasing a quality and precision of the breathing signal.

It should be noted that the structure data can be of the same or of different type (and/or data type) as the surface data. Accordingly, the structure data and the surface data can be captured using the same or different devices, such as e.g. imaging devices or other medical devices. Apart from the data type, the surface data and the structure data can refer to the same data or to different data.

According to an embodiment, the sequence of structure data covers approximately a complete breathing cycle. Therein, the complete breathing cycle may cover at least one entire breathing period, e.g. comprising an inhaling and an exhaling phase, in the breathing curve. Taking the entire breathing cycle into account for determining the motion trajectory allows to account for the entire movement of the structure during a breathing cycle. Hence, the movement of the structure can be described and/or approximated by the motion trajectory with high accuracy.

According to an embodiment, the sequence of structure data is acquired using at least one of a surface camera, a thermal camera, a marker device, a medical imaging device, and a breathing detector. Therein, the surface camera may refer to a 3D-camera, a stereo camera, a depth camera and/or an RGB-D camera. Further, the breathing detector may refer to any device suitable of determining and/or detecting the respiratory movement of the structure. Accordingly, the structure data can refer to camera data, image data, marker data and/or any other data describing or containing information about the respiratory movement and/or the position of the structure. Also, it should be noted that the structure data can refer to processed data and/or data that have been captured by any (or any combination) of the aforementioned means. For example, x-ray image data, CT scan data, MRI data or the like as well as a sequence thereof, such as e.g. 4DCT data, dynamic CT data, digitally reconstructed radiographic data or the like, can be further processed and/or analysed to generate the structure data and/or the sequence of structure data. Moreover, data from various sources can e.g. be combined and/or fused to generate the structure data and/or the sequence thereof.

According to an embodiment, the method further comprises determining and/or computing trajectory data indicative of a trajectory along which at least a part of the structure moves in the acquired sequence of structure data due to the respiratory movement. It should be noted that in the context of the present disclosure, the motion trajectory of the structure may approximate or be identical to the trajectory described by the trajectory data. Generally, the trajectory and/or motion trajectory can be a two-dimensional or three-dimensional trajectory in space. Further, the trajectory data may be regarded as tracking data indicative of the position of the structure over time. For example, the trajectory data can refer to at least a subset of the structure data, which can optionally be further processed. E.g. data points and/or at least a subset of the structure data in the sequence of structure data can be correlated with one another to determine the trajectory data.

According to an embodiment, the method further comprises determining, based on the determined trajectory data, a main motion axis, wherein the main motion axis is indicative of a main movement component of the respiratory movement of the at least part of the structure in the acquired sequence of structure data. Further, the motion trajectory of the structure may be derived from the trajectory data and/or the motion trajectory may be defined by the main motion axis as determined based on the trajectory data. The main movement component may refer to the spatial direction, in which the structure is predominantly displaced and/or predominantly moves during breathing. Hence, the main motion axis can accurately approximate the respiratory movement of the structure, thereby allowing to derive a precise breathing signal. Generally, the main motion axis can be determined based on processing and/or analysing the trajectory data, e.g. applying approximation techniques, statistical analysis, interpolation, extrapolation, fitting, minimization techniques or the like.

According to an embodiment, the main motion axis is determined based on a principal component analysis of the trajectory data. Generally, based on principal component analysis, PCA, the main motion axis and/or the main movement component can be determined with high precision in a fast manner. Therein, the main motion axis may be determined based on determining the axis of motion that approximates the trajectory data best, e.g. based on minimizing the sum of square errors and/or maximizing the variances of the trajectory data. By way of example, the first principal component of the respiratory movement of the structure may be determined based on analysing the trajectory data using PCA. The main motion axis may in turn be defined by and/or refer to the first principal component. However, also the second principal component and/or the third principal component may be taken into account for determining the main motion axis. Accordingly, the main motion axis may be defined by the first principal component in combination with the second and/or third principal component.

According to an embodiment, the method further comprises:
   acquiring and/or capturing at least one further surface data, e.g. temporally succeeding the surface data, representative, descriptive and/or indicative of at least one further position of the surface region of the patient (e.g. a further position in space);
   computing, determining and/or calculating at least one further intersection (e.g. in space) of the determined motion trajectory and the at least one further acquired surface data;
   determining at least one further breathing signal of the patient based on the computed at least one further intersection; and
   determining a breathing curve of the patient based on the determined breathing signal and the determined at least one further breathing signal.

The further surface data may e.g. be acquired at a further time instant during the breathing motion other than a time instant at which the surface data are acquired. In other words, a sequence, series, and/or time series of two or more temporally successive surface data may be acquired. The surface data or the sequence thereof may refer to a live sequence or live surface data, or it may have been captured and/or acquired previously, and e.g. stored on a data storage. Generally, the sequence of surface data can comprise first surface data indicative of a first position of the surface region in space at a first time instant and second surface data indicative of a second position of the surface region in space at a second time instant different from the first time instant. The intersection of each of the surface data and/or the positions of the surface region in space with the motion trajectory can represent a phase in the breathing cycle, a breathing state, a breathing activity, a depth of inspiration and/or a breathing amplitude of the patient. Accordingly, based on the sequence of (live) surface data, a sequence of intersections, i.e. intersections over time (or at different times/time instants), can be determined, thereby allowing to determine a sequence of breathing signals over time (or at different times/time instants). Accordingly, the breathing signal and/or the breathing curve can be determined in real-time and/or near real-time. In turn, this makes the breathing signal and/or the breathing curve particularly valuable for many medical applications ranging from the mere monitoring of a patient's breathing activity, via surgical applications to radiotherapy applications.

With particular reference to radiotherapy applications, the breathing signal and/or the breathing curve may, for example, be used for guiding the patient to a depth of inspiration in a DIBH-based treatment. Optionally, a medical system, e.g. a radiation treatment apparatus, can be operated based on the breathing signal. For instance, emission of a radiation treatment beam by a radiation treatment apparatus can be triggered and/or controlled based on the breathing signal.

Also, a position of a tissue to be treated can be determined based on the breathing signal, e.g. using a model correlating a position and/or movement of the tissue to be treated with the breathing signal and/or the breathing curve, wherein the position of the tissue may refer to a target position of the radiation treatment beam. Therein, (internal) target motions can be gained via e.g. fluoro imaging and/or soft tissue tracking. The model can then be used during the treatment to predict the target's position by feeding in and/or based on the current breathing signal. Accordingly, based on the breathing signal and the model, a target position of the tissue to be treated can be determined. Further, the radiation treatment beam may then be adjusted and/or positioned based on the breathing signal and/or the radiation treatment apparatus may be triggered and/or operatively controlled based on the breathing signal.

Further, it should be noted that the motion trajectory of the structure can be determined during a learning phase, such as e.g. during radiation treatment planning and/or before initiating the actual radiation treatment. Once the motion trajectory is determined, (live) surface data may be used to determine the breathing signal over time. However, the motion trajectory may also be adapted and/or updated during the actual treatment, e.g. to ensure correctness of the breathing signal. Updating the motion trajectory can, for instance, be done based on the acquired (live) surface data and/or any other structure data descriptive of the position of the structure.

According to an embodiment, the surface data is acquired using a surface camera. Alternatively or additionally, acquiring the surface data comprises capturing the surface region of the patient with at least one surface camera. Using a surface camera, such as a depth camera, a stereo camera, a 3D camera, and/or an RGB-D camera, allows to determine the breathing signal with high precision at increased comfort for the patient, e.g. because no reflective markers or the like may be required to capture the surface data. Further, additional radiation exposure can be avoided, e.g. compared to x-ray images or CT scans.

In a second aspect, the invention is directed to a computer program which, when running on and/or executed by at least one processor of at least one computer or when loaded into at least one memory of at least one computer, causes the at least one computer to perform the method according to the first aspect, as described above and in the following. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

A computer program stored on a disc is a data file, and when the file is read out and transmitted it becomes a data stream for example in the form of a (physical, for example electrical, for example technically generated) signal. The signal can be implemented as the signal wave which is described herein. For example, the signal and/or the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer, comprising at least one processor and at least one memory, wherein the program according to the second aspect is running on the processor or is loaded into the memory, or wherein the at least one computer comprises the computer-readable program storage medium according to the third aspect.

In a fifth aspect, the invention is directed to a medical system, comprising:
a) the at least one computer according to the fourth aspect;
b) at least one electronic data storage device storing the surface data and/or patient data, such as e.g. a voxel representation of at least a part of the patient, a clinical protocol file and/or an (optimized) irradiation treatment plan; and
c) a medical device for carrying out a medical procedure on the patient,
wherein the at least one computer is operably coupled to
the at least one electronic data storage device for acquiring and/or retrieving, from the at least one data storage device at least the surface data, and
the medical device for issuing a control signal to the medical device for controlling the operation of the medical device on the basis of the determined breathing signal, e.g. determined based on the method according to the first aspect.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling, on the basis of the breathing signal, at least one of the operation of the treatment beam source and the position of the patient support unit.

The present invention also relates to the use of any of the first to fifth aspect. Particularly, the invention also relates to the use of the method according to the first aspect, the program according to the second aspect, the computer-readable medium according to the third aspect and/or the computer according to the fourth aspect in the medical system or any embodiment thereof according to the fifth aspect.

Moreover, it is emphasized that features, functions, elements and/or steps, which are described above and in the following with reference to one aspect of the invention, equally apply to any other aspect of the invention described above and in the following. Particularly, features and/or steps, as described above and in the following, with reference to the method according to the first aspect, equally apply the computer program according to the second aspect, to the computer-readable medium according to the third aspect, to the computer according to the fourth aspect and/or to the medical system according to the fifth aspect, and vice versa.

It is emphasized, however, that the invention as described with reference to any of the first to fifth aspect does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to any non-invasive medical application and merely relates to a data processing method. For this reason alone, no surgical or therapeutic activity and in particular no surgical or therapeutic step is necessitated or implied by carrying out the invention.

These and other aspects of the invention will be apparent from and elucidated with reference to the embodiments described hereinafter.

DEFINITIONS

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably coupled to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: elekta.com and varian.com.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent exemplary embodiments of the invention. The scope of the invention is however not limited to the specific features disclosed in the context of the figures, wherein.

The figures are schematic only and not true to scale. In principle, identical or like parts, elements and/or steps are provided with identical or like reference symbols in the figures.

DESCRIPTION OF EMBODIMENTS

Figure 1:
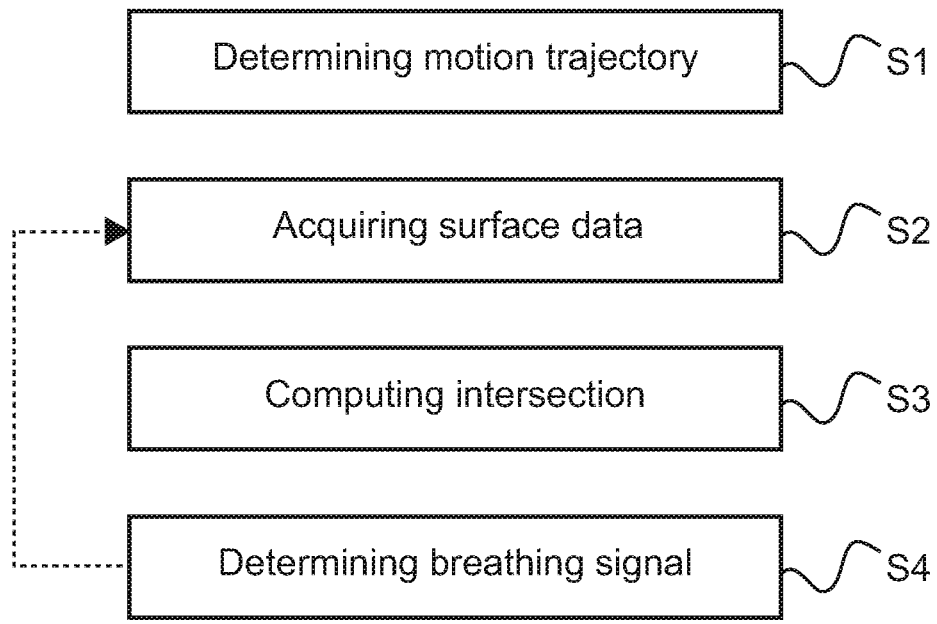
FIG. 1 shows a flowchart illustrating steps of a method of determining a breathing signal of a patient according to an exemplary embodiment of the invention.

FIG. 1 shows a flow chart illustrating the basic steps of the computer-implemented medical method of determining a breathing signal 202 and/or a breathing curve 200 (see FIG. 4) of a patient 100 (see FIG. 3) according to an exemplary embodiment and/or according to the first aspect.

Step S1 comprises determining a motion trajectory 120 (see FIG. 3) of a structure 104 (see FIG. 3) associated with at least one body part of the patient 100, wherein the motion trajectory 120 is indicative of a respiratory movement of the structure 104 and/or the at least one body part.

Therein, step S1 may comprise retrieving the motion trajectory 120 and/or trajectory data indicative of the motion trajectory 120 from a data storage. Accordingly, the motion trajectory 120 may be pre-defined.

Alternatively or additionally, the motion trajectory 120 may be determined based on structure data 51 (see FIG. 3), as will be described in more detail with reference to FIGS. 2 to 4.

Optionally, in step S1 a motion axis 110 indicative of the respiratory movement of at least a part of the structure 104 can be determined and/or defined based on the motion trajectory. The motion axis 110 may be a vertical or non-vertical axis with respect to a vertical axis 130 (see FIG. 3) of the patient 100 parallel to an anterior-posterior direction. Particularly, the motion axis 110 may take into account a respiratory movement of the structure 104 in anterior-posterior and in cranial-caudal direction of the patient 100. For example, the motion axis 110 and the vertical axis 130 of the patient 100 may enclose an angle of about 35° to about 55°, preferably about 40° to about 50°. The angle may, for example, be measured in a plane of a longitudinal axis and the vertical axis 130 of the patient 100.

In step S2, surface data 50 (see FIG. 3), such as e.g. image data, representative of a position of a surface region 106 of the patient 100 in space, e.g. at time instant during the breathing motion, are acquired. Optionally, this may comprise capturing the surface data 50, e.g. with a surface camera and/or any other type of device capable of capturing surface data 50 describing and/or containing information about the position of the surface region 106 in space.

In step S3, an intersection (in space) of the determined motion trajectory 120 and the acquired surface data 50 (and/or the surface region 106 represented by the surface data) is calculated. Optionally, intersection data descriptive of the intersection may be determined in step S3.

Based on the intersection, a breathing signal 202 (see FIG. 4) of the patient 100 is determined in step S4, which can represent a breathing amplitude, a breathing state, a depth of inspiration and/or a breathing activity of the patient 100 at a specific time and/or time instant.

As indicated by the arrow in FIG. 1, steps S2 to S4 can be iteratively repeated, thereby allowing to determine a sequence of temporally successive breathing signals 202 and/or a breathing curve 200 of the patient 100.

Figure 2:
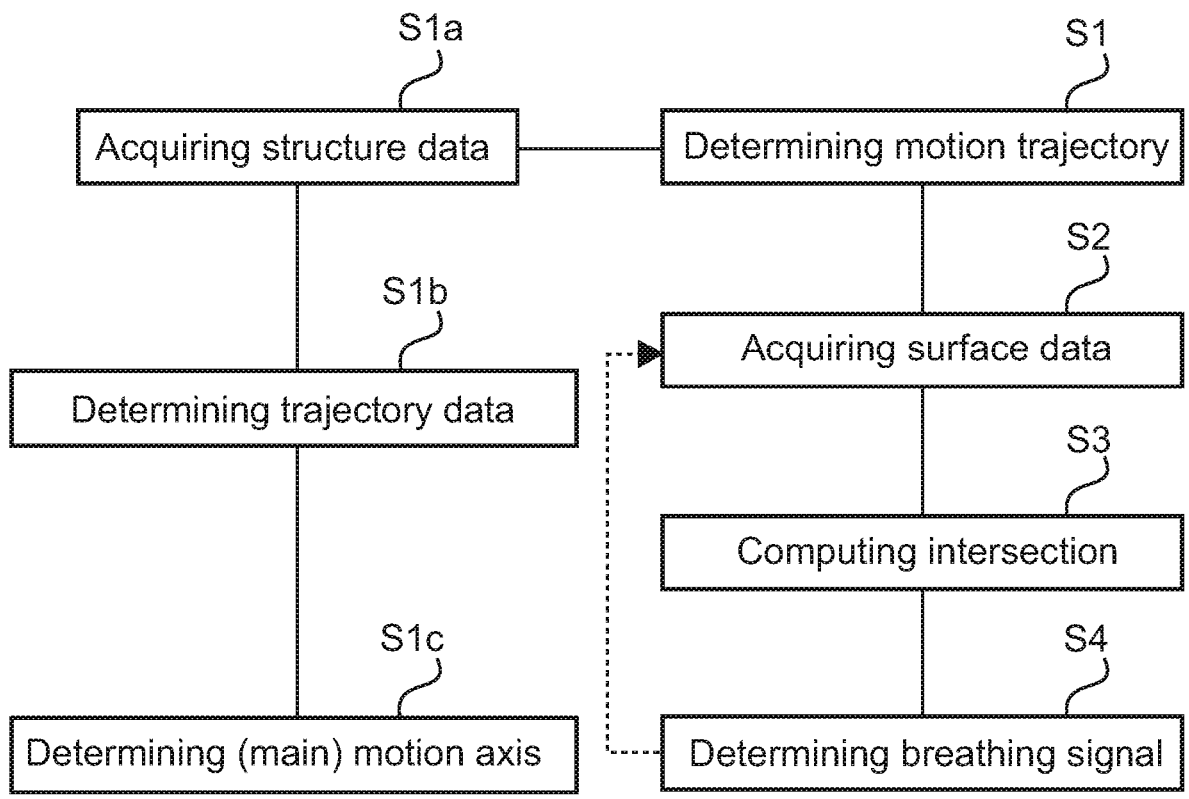
FIG. 2 shows a flowchart illustrating steps of a method of determining a breathing signal of a patient according to an exemplary embodiment of the invention.

FIG. 2 shows a flowchart illustrating steps of a method of determining a breathing signal 202 (see FIG. 4) of a patient 100 according to an exemplary embodiment of the invention. If not stated otherwise, steps S1 to S4 of FIG. 2 are identical to steps S1 to S4 described with reference to FIG. 1. FIG. 3 illustrates some steps of the method according to FIGS. 1 and 2. FIG. 4 illustrates a breathing signal 202 and/or a breathing curve 200 determined based on the method of FIGS. 1 and 2.

Figure 3:
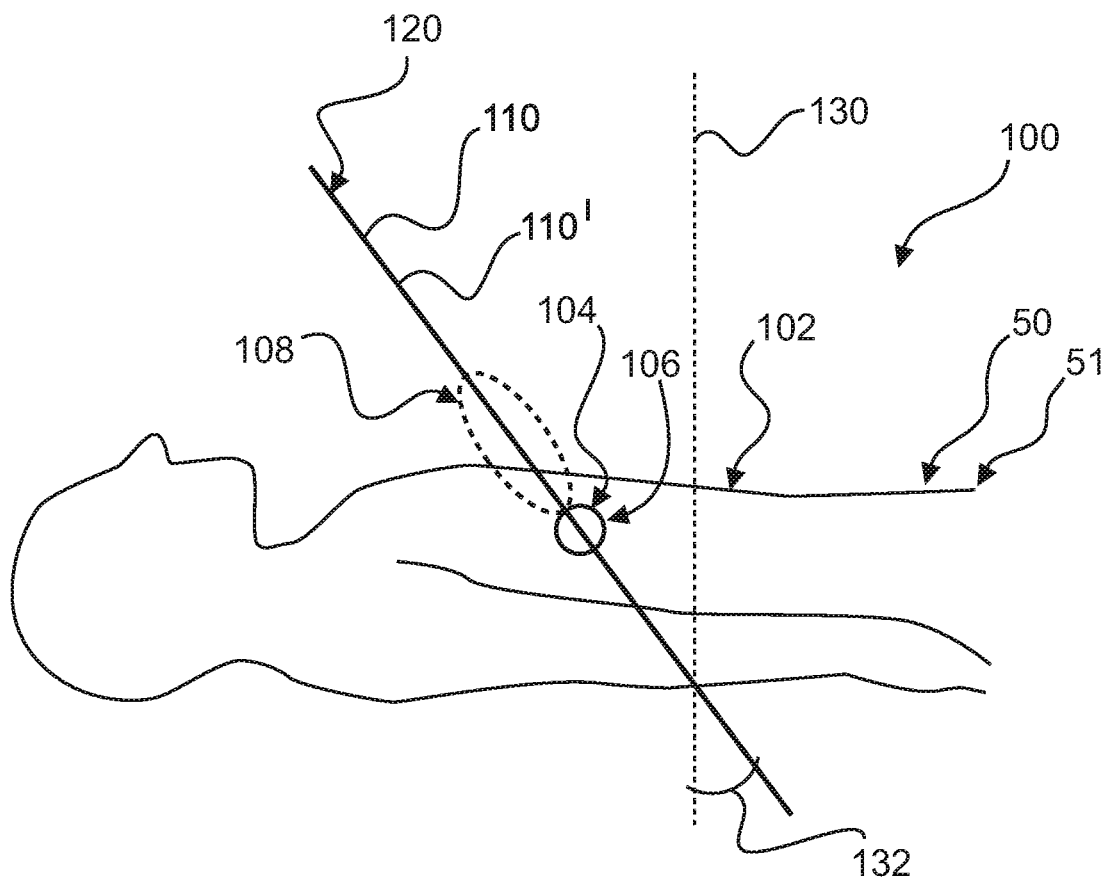
FIG. 3 illustrates some steps of the method according to FIGS. 1 and 2.

Specifically, FIG. 3 illustrates structure data 51 as well as surface data 50, as used in the context of the present disclosure. Accordingly, in the example depicted in FIG. 3, both the structure data 51 and the surface data 50 are of the same data type and exemplary acquired by means of a surface camera. It should be noted, however, that the structure data 51 can be of different type compared to the surface data 50. Hence, the structure data 51 and the surface data 50 can be captured with different means. Specifically, the structure data 51 and the surface data 50 can be captured with any one or more of a surface camera, a thermal camera, a marker device, a medical imaging device, and a breathing detector, as described in the summary part of the present disclosure.

Further, it should be noted that in the example shown in FIG. 3, the structure 104 associated with the at least one body part of the patient 100, for which the motion trajectory 120 is determined in step S1, refers to at least a part of the surface region 106 that is intersected with the motion trajectory 120 in step S3. Alternatively, any other structure 106 that moves in accordance with a breathing motion of the patient 100 can be used, which may differ from the surface region 106. Generally, the surface region 106 and/or the structure 104 may refer to an arbitrary area or region of interest, based on which the breathing signal 202 is determined. Further, the at least one body part in the example of FIG. 3 can, for instance, refer to the patient's torso and/or the surface region 106.

In FIG. 2, the determination of the motion trajectory 120 is exemplary further illustrated by optional steps S1a to S1c. The motion trajectory 120 may, for instance, be determined in a learning phase.

In step S1a, at least two temporally successive structure data 51 and/or a sequence of structure data 51 is acquired. Each of the acquired structure data 51 is representative of a position of at least a part of the structure 104 in space, e.g. at a certain time and/or time instant.

In step S1b, trajectory data indicative of a trajectory 108 along which at least a part of the structure 104 moves and/or is displaced in the sequence of structure data 51 is determined. Optionally, this may comprise tracking the structure 104 and/or the position thereof, e.g. such that the trajectory data may be given as two-dimensional or three-dimensional spatial coordinates as a function time. As shown in FIG. 3, the trajectory 108 of the structure 104 and/or at least a part thereof may be hysteresis like and/or elliptically. Any other trajectory 108, however, is conceivable. The trajectory data may be indicative of the trajectory 108 in two or three spatial directions. In other words, the trajectory data may be two-dimensional or three-dimensional trajectory data. For instance, the (actual) trajectory 108 may be projected into a plane held by a longitudinal axis and the vertical axis 130 of the patient 100 to generate two-dimensional trajectory data.

Further, in step S1c, a motion axis 110 is determined based on the trajectory data and/or the trajectory 108. The motion axis 110 can accurately approximate the movement and/or displacement of the structure 104 caused by the breathing of the patient 100. As shown in FIG. 3, the motion axis 110 is tilted in cranial-caudal direction with respect to a vertical axis 130 of the patient and/or transverse to the cranial-caudal direction, thereby allowing to precisely approximate the respiratory movement of the structure 104.

The motion axis 110 may enclose an angle 132 (of e.g. about 30° to 50°) with the vertical axis 130 along the cranial-caudal direction of the patient 100 and/or parallel to the longitudinal axis of the patient. Hence, the motion axis 110 may lay in the plane held by the longitudinal axis and the vertical axis 130 of the patient 100. Also, the motion axis 110 may be skew with respect to the vertical axis 130, i.e. it may be tilted in cranial-caudal (or longitudinal) direction and transverse thereto.

Generally, the motion axis 110 may describe one or more movement components related to one or more spatial directions the structure 104 is displaced during breathing. Particularly, the motion axis 110 may refer to a main motion axis 110' indicative of a main movement component of the respiratory movement of the structure 104. For instance, the main motion axis 110' may be determined in step S1c based on the trajectory data using principal component analysis. For instance, the main motion axis 110' may be defined by the first principal component (optionally also the second and/or third principal component) as determined based on analysing the trajectory data using PCA, as described in detail in the summary part of the present disclosure.

Further, the motion trajectory 120 of the structure 104 may be determined in step S1c based on the determined motion axis 110 and/or the determined main motion axis 110'. In this context, the motion trajectory 120 may be defined by and/or may be given by the motion axis 110 and/or the main motion axis 110'.

Once the motion trajectory 120 is determined, the method of FIG. 2 can continue with steps S2 to S4 as described with reference to FIG. 1. By iteratively repeating steps S2 to S4, a sequence of surface data 50 over time is acquired, a sequence of intersections is computed over time, and a sequence of breathing signals 202 is determined over time. Therein, the breathing signal 202 over time allows determining and/or provides a breathing curve 200 as exemplary shown in FIG. 4. Specifically, FIG. 4 shows the breathing curve 200 as a breathing amplitude in arbitrary units as a function of time in arbitrary units. A point on the breathing curve 200 represents the breathing signal 202, which may be given as a breathing amplitude A at a time t.

Figure 4:
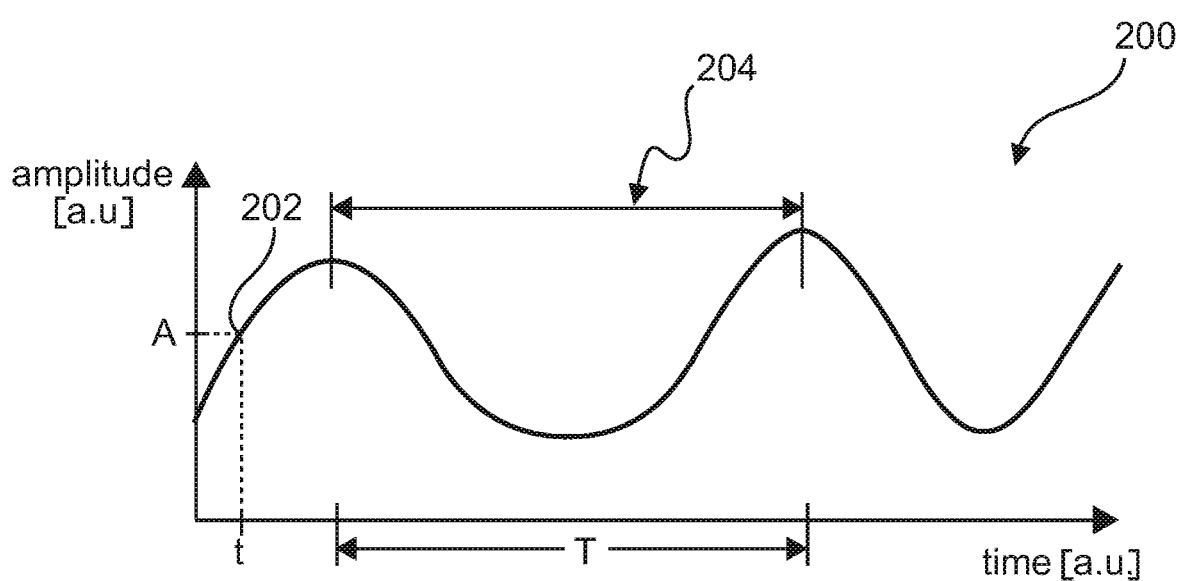
FIG. 4 illustrates a breathing signal and/or a breathing curve determined based on the method of FIGS. 1 and 2.

Further, FIG. 4 illustrates a breathing cycle 204, which corresponds to a part of the breathing curve 200 covering one breathing period (and/or a respiratory cycle), e.g. between two consecutive maxima as shown in FIG. 4. It should be noted that the sequence of structure data 51 acquired in step S1a may preferably cover a complete breathing cycle 204, although this may not be required to accurately determine the breathing signal 202.

Figure 5:
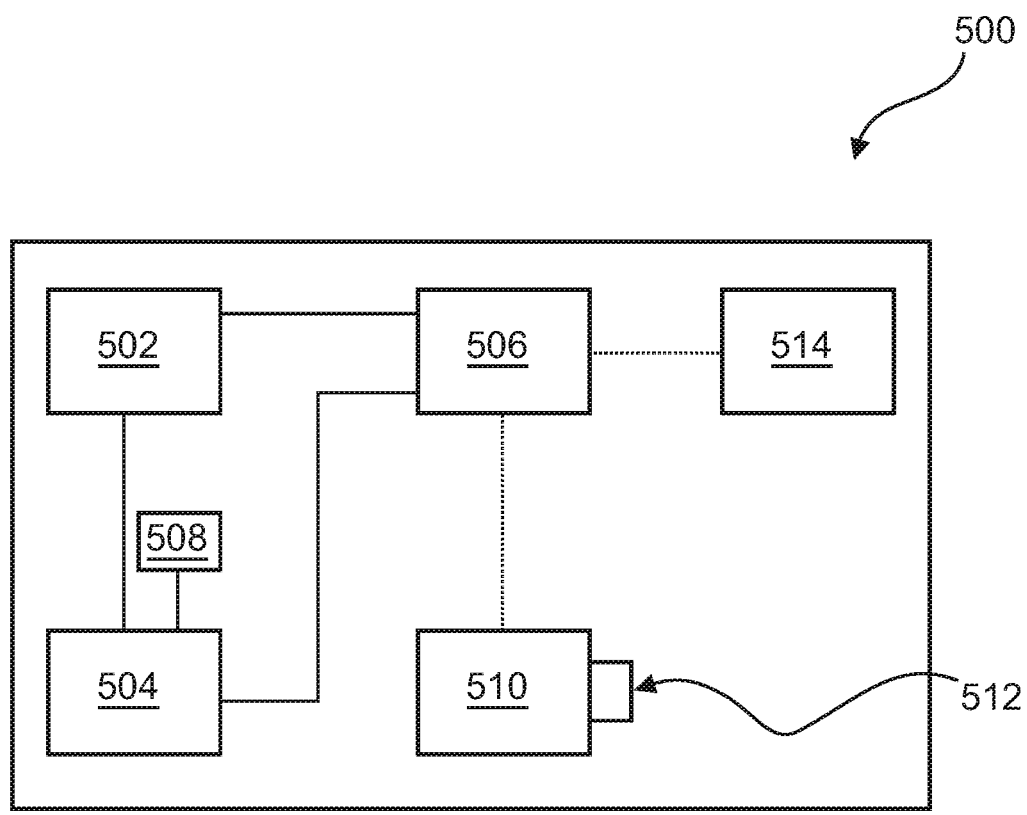
FIG. 5 schematically shows a medical system according to an exemplary embodiment of the invention.

FIG. 5 shows schematically a medical system 500 according to an exemplary embodiment of the invention and/or according to the fifth aspect. The system is in its entirety identified by reference numeral 500 and comprises a computer 502, an electronic data storage device (such as a hard disc) 504 for storing at least the surface data 50, and a medical device 506, e.g. for carrying out a medical procedure, particularly an irradiation treatment. The components of the medical system 500 have the functionalities and properties explained above and in the following with regard to the fifth and/or any other aspect of the present disclosure. Particularly, the at least one computer 502 is operably coupled to the at least one electronic data storage 504 device for acquiring, from the at least one data storage device 504, at least the surface data 50. The system 500 may further comprise a surface camera 508 for capturing the structure data 51 and/or the surface data 50.

Further, computer 502 is coupled to the medical device 506 for issuing a control signal to the medical device 506 for controlling the operation of the medical device 506 on the basis of the breathing signal 202, as described above and in the following.

The medical system 500 and/or the medical device 506 of the system 500 comprises a radiation treatment apparatus 510 comprising a treatment beam source 512 and a patient support unit 514, wherein the at least one computer 502 is operably coupled to the radiation treatment apparatus 510 for issuing a control signal to the radiation treatment apparatus 510 for controlling, on the basis of the breathing signal 202, at least one of the operation of the treatment beam source 512 and the position of the patient support unit 514.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method executed on at least one processor of at least one computer for issuing a control signal useable by an associated medical device for controlling operation of the medical device, the method comprising:
    determining, by the at least one processor, a motion trajectory of a structure associated with at least one body part of a patient, wherein the motion trajectory is indicative of a respiratory movement of the structure;
    acquiring, at the at least one processor, surface data representative of a position of a surface region of the patient;
    computing, by the at least one processor, an intersection of the determined motion trajectory and the acquired surface data;
    determining, by the at least one processor, a breathing signal of the patient based on the computed intersection, wherein the breathing signal is indicative of a breathing state of the patient; and
    issuing, by the at least one processor, the control signal to the associated medical device for controlling operation of the medical device, based on the determined breathing signal of the patient, for carrying out a medical procedure on the patient.

2. The method according to claim 1, wherein the motion trajectory is indicative of the respiratory movement of at least a part of the structure in an anterior-posterior direction and in a cranial-caudal direction of the patient.

3. The method according to claim 1, wherein determining the motion trajectory of the structure comprises defining a motion axis approximating the respiratory movement of at least a part of the structure.

4. The method according to claim 3, wherein the motion axis and a vertical axis of the patient enclose an angle of about 35° to about 55°.

5. The method according to claim 4, wherein the angle is about 40° to about 50°.

6. The method according to claim 1, wherein determining the motion trajectory comprises:
    acquiring, at the at least one processor, a sequence of at least two temporally successive structure data, wherein each structure data is representative of a position of at least a part of the structure in a breathing cycle of the patient.

7. The method according to claim 6, wherein the sequence of the at least two temporally successive structure data covers approximately a complete breathing cycle.

8. The method according to claim 6, wherein the acquiring the sequence of the at least two temporally successive structure data comprises acquiring the sequence of the at least two temporally successive structure data using one or more of a surface camera, a thermal camera, a marker device, a medical imaging device, and/or a breathing detector.

9. The method according to claim 6, further comprising:
    determining, by the at least one processor, trajectory data indicative of a trajectory along which at least a part of the structure moves in the acquired sequence of the at least two temporally successive structure data.

10. The method according to claim 9, further comprising:
    determining, by the at least one processor and based on the determined trajectory data, a main motion axis,
    wherein the main motion axis is indicative of a main movement component of the respiratory movement of at least the part of the structure in the acquired sequence of the at least two temporally successive structure data.

11. The method according to claim 10, wherein the determining the main motion axis comprises determining the main motion axis based on a principal component analysis of the trajectory data.

12. The method according to claim 1, further comprising:
    acquiring, at the at least one processor, at least one further surface data representative of at least one further position of the surface region of the patient;
    computing, by the at least one processor, at least one further intersection of the determined motion trajectory and the at least one further acquired surface data;
    determining, by the at least one processor, at least one further breathing signal of the patient based on the computed at least one further intersection;
    determining, by the at least one processor, a breathing curve of the patient based on the determined breathing signal and the determined at least one further breathing signal; and
    issuing, by the at least one processor, the control signal to the associated medical device for controlling the operation of the medical device based on the determined breathing curve of the patient.

13. The method according to claim 1, wherein the acquiring the surface data comprises acquiring the surface data using a surface camera; and/or wherein the acquiring the surface data comprises capturing the surface region of the patient with the surface camera.

14. A non-transitory computer readable storage medium storing a program comprising program instructions that, when executed on at least one processor of a computer or loaded onto the at least one processor of the computer, causes the computer to issue a control signal useable by an associated medical device for controlling operation of the medical device by:
- determining a motion trajectory of a structure associated with at least one body part of a patient, wherein the motion trajectory is indicative of a respiratory movement of the structure;
- acquiring surface data representative of a position of a surface region of the patient;
- computing an intersection of the determined motion trajectory and the acquired surface data;
- determining a breathing signal of the patient based on the computed intersection, wherein the breathing signal is indicative of a breathing state of the patient; and
- issuing the control signal to the associated medical device for controlling operation of the medical device, based on the determined breathing signal of the patient, for carrying out a medical procedure on the patient.

15. A medical system, comprising:
at least one computer;
at least one electronic data storage device storing at least surface data representative of a position of a surface region of a patient; and
a medical device for carrying out a medical procedure on the patient,
wherein the at least one computer is operable to:
- determine a motion trajectory of a structure associated with at least one body part of the patient, wherein the motion trajectory is indicative of a respiratory movement of the structure;
- acquire, from the at least one electronic data storage device, the surface data representative of the position of the surface region of the patient;
- compute an intersection of the determined motion trajectory and the acquired surface data;
- determine a breathing signal of the patient based on the computed intersection, wherein the breathing signal is indicative of a breathing state of the patient; and
- issue a control signal to the medical device for controlling operation of the medical device based on the determined breathing signal.

16. The medical system according to claim 15, wherein the medical device comprises:
a radiation treatment apparatus comprising a treatment beam source and a patient support unit,
wherein the at least one computer is operably coupled to the radiation treatment apparatus for issuing the control signal to the radiation treatment apparatus for controlling, based on the determined breathing signal, at least one of the operation of the treatment beam source or a position of the patient support unit.

17. The medical system according to claim 15, wherein the at least one computer is further operable to:
define a motion axis approximating the respiratory movement of at least a part of the structure.

18. The medical system according to claim 15, wherein the at least one computer is further operable to:
- acquire at least one further surface data representative of at least one further position of the surface region of the patient;
- compute at least one further intersection of the determined motion trajectory and the at least one further acquired surface data;
- determine at least one further breathing signal of the patient based on the computed at least one further intersection;
- determine a breathing curve of the patient based on the determined breathing signal and the determined at least one further breathing signal; and
- issue the control signal to the medical device for controlling the operation of the medical device based on the determined breathing curve of the patient.

19. The medical system according to claim 15, wherein the at least one computer is further operable to:
acquire a sequence of at least two temporally successive structure data, wherein each structure data is representative of a position of at least a part of the structure in a breathing cycle of the patient.

20. The medical system according to claim 19, wherein the at least one computer is further operable to:
- determine trajectory data indicative of a trajectory along which at least a part of the structure moves in the acquired sequence of the at least two temporally successive structure data; and
- determine, based on the determined trajectory data, a main motion axis, wherein the main motion axis is indicative of a main movement component of the respiratory movement of at least the part of the structure in the acquired sequence of the at least two temporally successive structure data.

* * * * *